(12) United States Patent
Komatsubara et al.

(10) Patent No.: US 9,113,612 B2
(45) Date of Patent: Aug. 25, 2015

(54) ABSORBENT ARTICLE FOR PET

(75) Inventors: Daisuke Komatsubara, Kagawa (JP);
Takeshi Ikegami, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 0 days.

(21) Appl. No.: 14/007,909

(22) PCT Filed: Mar. 13, 2012

(86) PCT No.: PCT/JP2012/056472
§ 371 (c)(1),
(2), (4) Date: Nov. 27, 2013

(87) PCT Pub. No.: WO2012/132890
PCT Pub. Date: Oct. 4, 2012

(65) Prior Publication Data
US 2014/0123913 A1 May 8, 2014

(30) Foreign Application Priority Data
Mar. 30, 2011 (JP) ................................. 2011-075849

(51) Int. Cl.
*A01K 23/00* (2006.01)
*A61F 13/62* (2006.01)
*A61F 13/15* (2006.01)

(52) U.S. Cl.
CPC ................ *A01K 23/00* (2013.01); *A61F 13/15* (2013.01); *A61F 13/622* (2013.01); *A61F 2013/15186* (2013.01)

(58) Field of Classification Search
USPC .......... 119/869, 867, 868, 850, 856; 604/358, 604/385.01–385.05, 385.11, 385.201, 604/385.23, 385.24, 386, 387, 389, 391
See application file for complete search history.

(56) References Cited

U.S. PATENT DOCUMENTS

| 3,848,599 | A | | 11/1974 | Schaar |
|---|---|---|---|---|
| 4,577,591 | A | * | 3/1986 | Wesseldine ................... 604/391 |
| 4,775,375 | A | * | 10/1988 | Aledo ............................ 604/378 |

(Continued)

FOREIGN PATENT DOCUMENTS

| JP | 2004-159592 A | 6/2004 |
|---|---|---|
| JP | 2005-229915 A | 9/2005 |

(Continued)

OTHER PUBLICATIONS

European Search Report from corresponding European application No. 12763577.9 dated Sep. 15, 2014 (4 pgs).

(Continued)

*Primary Examiner* — Trinh Nguyen
(74) *Attorney, Agent, or Firm* — Brinks Gilson & Lione

(57) ABSTRACT

An absorbent article for pets includes a top surface layer, a back surface layer, and an absorbent body, and is formed in a rectangular shape having opposing first and second end portions, and a pair of opposing side portions that are perpendicular to the first and second end portions, The top surface layer side of the first end portion is arranged on the body of the pet, and the top surface layer side of the second end portion is detachably attached to the back surface layer side of the first end portion when worn. The absorbent article includes a rectangular engaging member arranged on the back surface layer side of the first end portion; and a pair of folding line portions formed on the first end portion and constituting a point where the pair of opposing side portions begin to curve towards the front surface layer side.

7 Claims, 13 Drawing Sheets

(56) References Cited

U.S. PATENT DOCUMENTS

| | | | |
|---|---|---|---|
| 4,996,949 A * | 3/1991 | Wunderman et al. | 604/390 |
| 5,032,120 A * | 7/1991 | Freeland et al. | 604/385.27 |
| 5,397,318 A * | 3/1995 | Dreier | 604/385.19 |
| 5,555,847 A * | 9/1996 | Kelly | 119/850 |
| 5,895,382 A * | 4/1999 | Popp et al. | 604/385.21 |
| 5,954,015 A * | 9/1999 | Ohta | 119/850 |
| 6,248,097 B1 * | 6/2001 | Beitz et al. | 604/385.27 |
| 6,270,487 B1 * | 8/2001 | Sheehan et al. | 604/385.28 |
| 6,371,950 B1 * | 4/2002 | Roslansky et al. | 604/385.19 |
| 6,533,765 B1 * | 3/2003 | Blaney et al. | 604/385.26 |
| 6,897,351 B2 * | 5/2005 | Nakaoka et al. | 604/381 |
| 6,921,394 B2 * | 7/2005 | Sayama et al. | 604/385.19 |
| 8,361,047 B2 * | 1/2013 | Mukai et al. | 604/385.27 |
| 8,568,379 B2 * | 10/2013 | LaVon et al. | 604/385.04 |
| 2003/0069555 A1 * | 4/2003 | Erdman | 604/369 |
| 2005/0154367 A1 * | 7/2005 | Ikegami | 604/389 |
| 2007/0129702 A1 | 6/2007 | Gribben | |
| 2010/0094235 A1 | 4/2010 | Solomon et al. | |
| 2011/0209675 A1 * | 9/2011 | Esperon | 119/868 |
| 2014/0107606 A1 * | 4/2014 | Komatsubara et al. | 604/391 |
| 2014/0109843 A1 * | 4/2014 | Komatsubara et al. | 119/869 |
| 2014/0290589 A1 * | 10/2014 | Komatsubara et al. | 119/869 |

FOREIGN PATENT DOCUMENTS

| | | |
|---|---|---|
| JP | 2007-20533 A | 2/2007 |
| JP | 3141580 | 4/2008 |
| WO | WO 2010/127063 A1 | 11/2010 |

OTHER PUBLICATIONS

International Search Report based on corresponding PCT application No. PCT/JP2012/056472 dated May 15, 2012 (4 pgs).

* cited by examiner

ABSORBENT ARTICLE FOR PET

RELATED APPLICATION

This application is a 35 U.S.C. §371 national phase filing of International Patent Application No. PCT/JP2012/056472 filed Mar. 13, 2012, to which priority is claimed under 35 U.S.C. §120 and through which priority is claimed under 35 U.S.C. §119 to Japanese Patent Application No. 2011-075849, filed Mar. 30, 2011.

TECHNICAL FIELD

The present invention relates to an absorbent article for pet, which is used in a state of being wrapped around the waist of a pet such as a dog or cat.

BACKGROUND ART

Heretofore, a disposable diaper for pet used for a pet such as a dog or cat has been proposed. Such a disposable diaper for pet catches feces and urine of the pet by covering the anus and the urethral opening positioned in the crotch between the hind legs when worn.

Some pets (for example a miniature dachshund) have the urethral opening more in front than in the crotch between the hind legs. In addition, male dogs have the urethral opening more in front than female dogs. If the disposable diaper for pet is used for pets having the urethral opening more in front than in the crotch between the hind legs, the urethral opening may not be covered by the diaper and urine may leak.

Given this, an absorbent article for pet that is configured in a belt-like shape and worn in a state of being wrapped around the pet's waist is proposed (for example see Patent Document 1).

Such an absorbent article for pet configured in a belt-like shape can assuredly cover the urethral opening, regardless of position of the urethral opening.

Patent Document 1: Japanese Unexamined Patent Application Publication No. 2007-20533

DISCLOSURE OF THE INVENTION

Problems to be Solved by the Invention

The absorbent article for pet used in a state of being wrapped around the pet's waist, as proposed in Patent Document 1, is put on the pet in the following steps, for example.

First, a first end portion located on a first end side of the absorbent article for pet in a longitudinal direction is placed on the pet's back, and the first end portion is held by one hand of a user, thereby keeping the first end portion in close contact with the pet's back. Next, in a state where the first end portion is held by one hand, a second end portion located on a second end side of the absorbent article for pet is held by the other hand and wrapped around the pet's body to cover the pet's abdomen. Then the second end portion of the absorbent article for pet is pulled to bring a side portion of the absorbent article for pet in a longitudinal direction into close contact with the pet's waist, and in this state, an inner surface of the second end portion of the absorbent article for pet is engaged with an outer surface of the first end portion. The absorbent article for pet can thus be maintained in a state of being appropriately wrapped around the pet's waist.

Here, the first end portion and the second end portion of the absorbent article for pet are joined by engaging a hook member provided on the outer surface of the first end portion with a loop member provided on the inner surface of the second end portion, or by arranging an adhesive tape on the outer surface of the first end portion and attaching the inner surface of the second end portion to the adhesive tape.

However, in a case in which the hook member or the adhesive tape is arranged on the outer surface of the first end portion of the absorbent article for pet, if a pet moves in a state where the first end portion is held by one hand to be kept in close contact with the pet's back as described above, the pet's hair may become entangled with the hook member or adhesive. If the pet's hair is entangled with the hook member or the adhesive tape, the force of engaging the first end portion with the second end portion of the absorbent article for pet is weakened. As a result, the pet's hair is damaged.

Therefore, an object of the present invention is to provide an absorbent article for pet, which can reduce entanglement of pet's hair when being worn.

Means for Solving the Problems

The present invention relates to an absorbent article for pet, in which the absorbent article includes: a liquid permeable top surface layer; a liquid impermeable back surface layer; and an absorbent core arranged between the top surface layer and the back surface layer; in which the absorbent article is formed in a rectangular shape having first and second end portions opposed to each other, and a pair of side portions opposed to each other and orthogonal to the first and second end portions, and in which, in a state of being wrapped around a pet's waist, a top surface layer side of the first end portion is arranged to face the pet's body, and the top surface layer side of the second end portion is removably attached to a back surface layer side of the first end portion. The absorbent article for pet further includes: a locking member arranged on the back surface layer side of the first end portion, and formed in a rectangular shape, in which a longitudinal direction of the locking member extends along a width direction of the absorbent article for pet; and a pair of folding-line portions formed in the first end portion, in which a pair of side portions side of the first end portion is bent at the pair of folding-line portions toward the top surface layer side.

It is preferable for the pair of folding-line portions to be formed in the locking member, and to extend along a longitudinal direction of the absorbent article for pet.

It is preferable for length between the pair of folding-line portions to be larger than width of the absorbent core.

It is preferable for the absorbent article for pet to further include: a pair of side sheets respectively arranged on an outer surface side of the top surface layer in the pair of side portions along a longitudinal direction of the absorbent article for pet, in which an outer edge is joined to the top surface layer or the back surface layer, and at least a part of an inner edge is a free end; a pair of first elastic members arranged in a stretched state in a vicinity of the inner edge of the pair of side sheets; and a pair of pocket portions formed between an inner surface of the pair of side sheets and an outer surface of the top surface layer.

It is preferable for the absorbent article for pet to further include a pair of second elastic members arranged in a stretched state in each of the pair of side portions.

It is preferable for the locking member to be attached at a separated position within a predetermined distance from a side edge of the first end portion.

It is preferable for the absorbent article for pet to further include a rectangular base material arranged in the first end portion, and it is preferable for the pair of folding-line portions to be formed in the base material.

Regarding bending rigidity of the locking member being bent in a longitudinal direction, it is preferable for bending resistance to be 60 mm to 200 mm, which is measured with a bending resistance method A (45-degree cantilever method) as defined in L1084 (testing method for flocked fabrics).

Effects of the Invention

The absorbent article for pet according to the present invention can, when worn, reduce the entanglement of pet hair.

Figure 1:
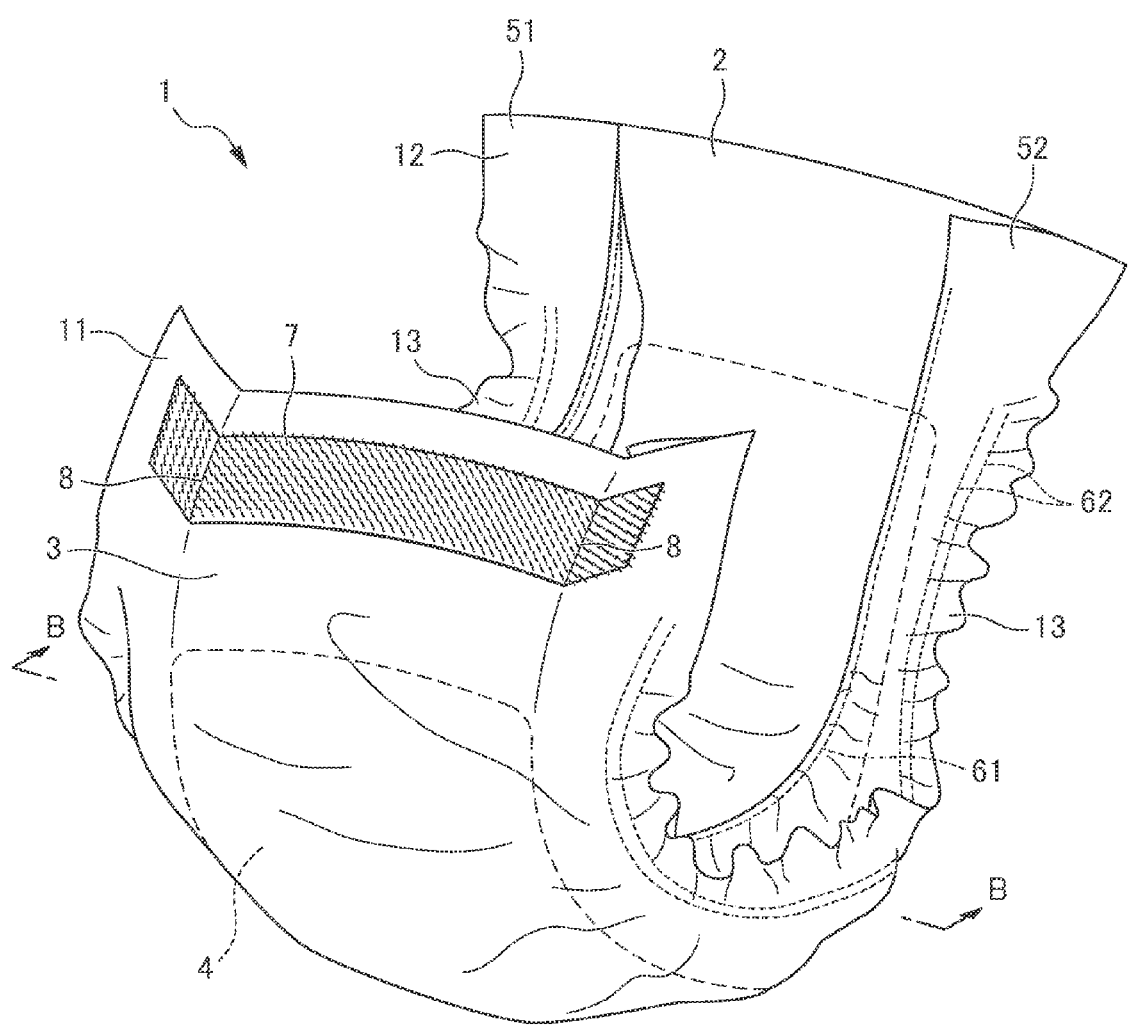
FIG. 1 is a perspective view showing an absorbent article for pet according to a first embodiment of the present invention.

EXPLANATION OF REFERENCE NUMERALS 1 absorbent article for pet
2 top sheet (top surface layer)
3 back surface layer
4 absorbent core
7 hook tape (locking member)
8 folding-line portion
9 base material
11 first end portion
12 second end portion
14 pocket portion
15 pocket portion
17 side portion
51 front side sheet (side sheet)
52 rear side sheet (side sheet)
61 first elastic member (elastic member)
62 second elastic member (elastic member)

PREFERRED MODE FOR CARRYING OUT THE INVENTION

Embodiments of the absorbent article for pet according to the present invention will be described hereinafter with reference to the drawings.

First, the absorbent article for pet according to the first embodiment will be described with reference to FIGS. 1 to 6.

Figure 2:
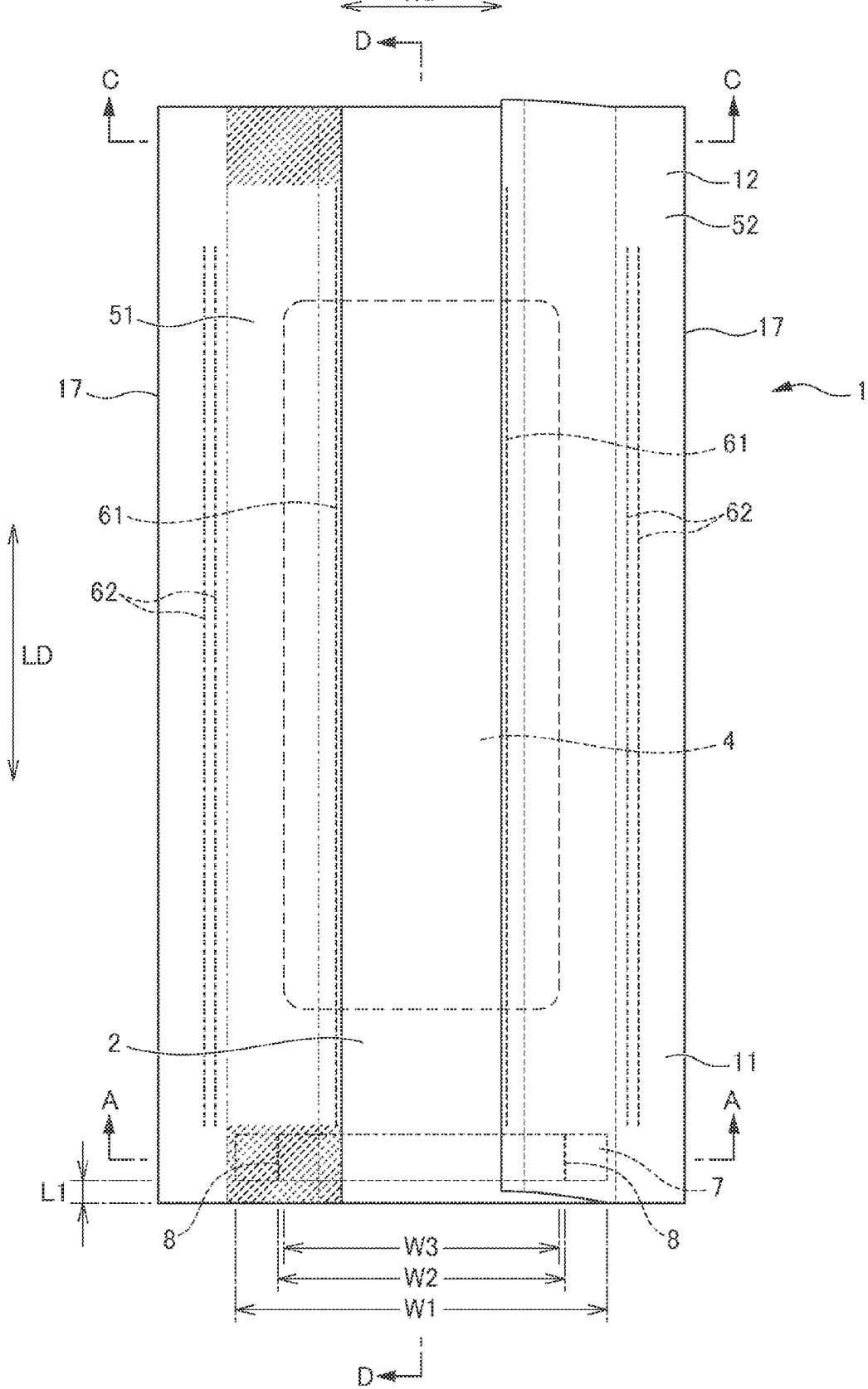
FIG. 2 is a plan view of the absorbent article for pet according to the first embodiment viewed from a top surface layer side.

As shown in FIGS. 1 and 2, an absorbent article for pet 1 according to the first embodiment is configured in a rectangular shape with a first end portion 11 and a second end portion 12 facing each other and a pair of side portions 17 facing each other orthogonally to the first end portion 11 and the second end portion 12, the absorbent article for pet 1 being worn in a state of being wrapped around the pet's waist. The absorbent article for pet 1 is especially preferably used for a pet having the urethral opening located further toward the front than the crotch between the hind legs (such as for a miniature dachshund).

The absorbent article for pet 1 includes, as shown in FIGS. 1 to 6: a top sheet 2 constituting a liquid permeable top surface layer; a back sheet 31 and a waterproof sheet 32 constituting a liquid impermeable back surface layer 3; an absorbent core 4; a pair of side sheets 51, 52; first elastic members 61 and second elastic members 62 as elastic members; a hook tape 7 as a locking member; and a pair of folding-line portions 8 formed in the hook tape 7.

The top sheet 2 is configured in a rectangular shape. The top sheet 2 mainly composes a surface of a side in contact with the pet's body. As the top sheet 2, a perforated or non-perforated nonwoven fabric or a porous plastic sheet can be used. In the first embodiment, the back sheet 31 is composed of a nonwoven fabric with which a hook portion 72 (to be described later) can engage.

Figure 4:
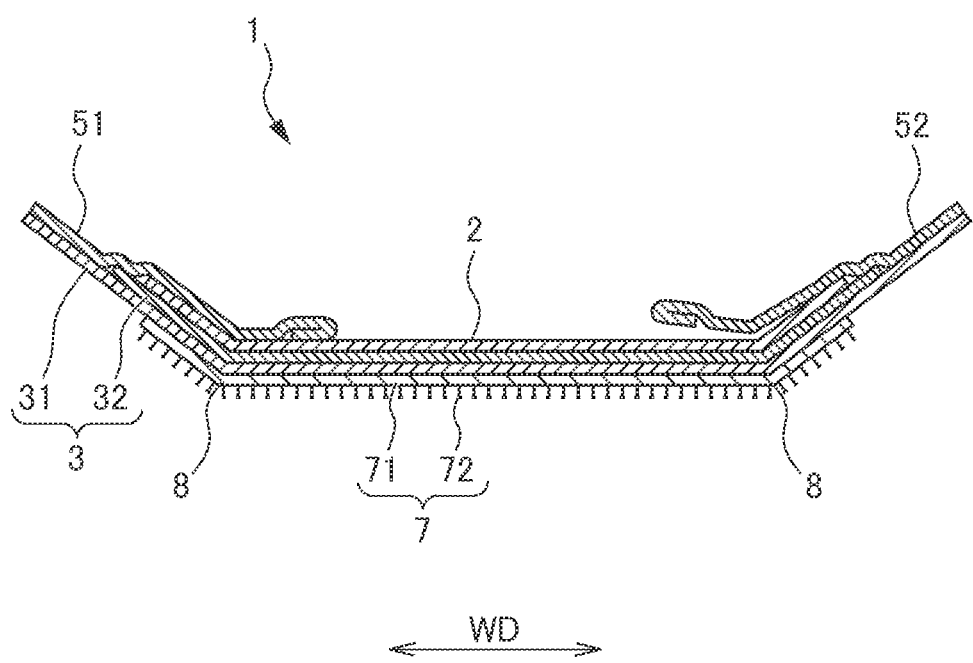
FIG. 4 is a cross-sectional view taken along the line A-A of FIG. 2.
Figure 5:
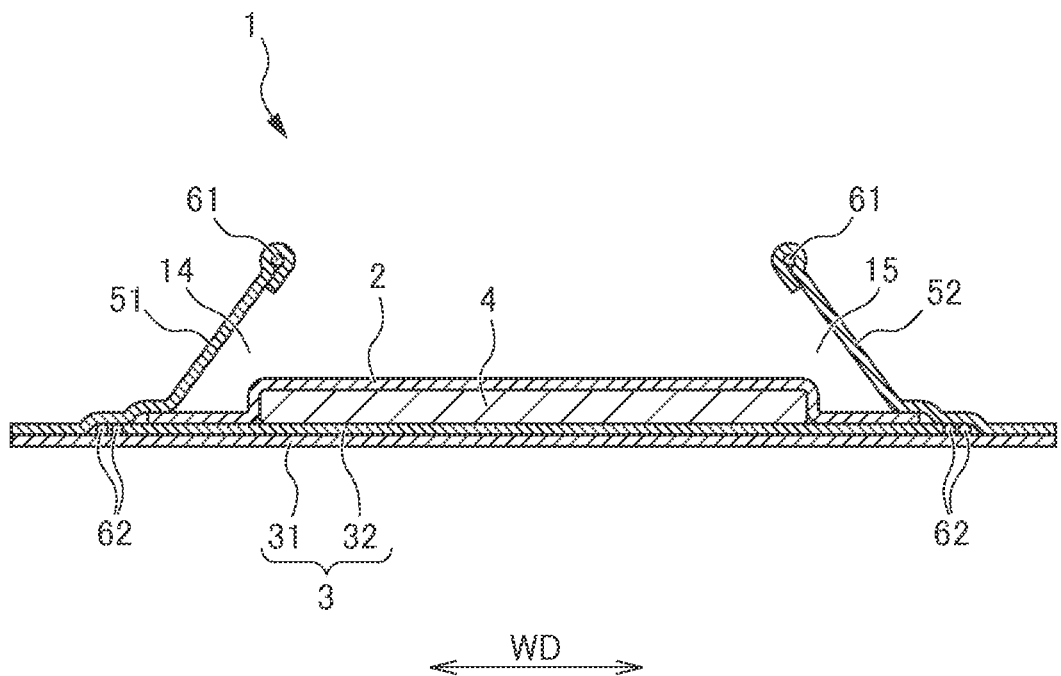
FIG. 5 is a cross-sectional view taken along the line B-B of FIG. 1.
Figure 6:
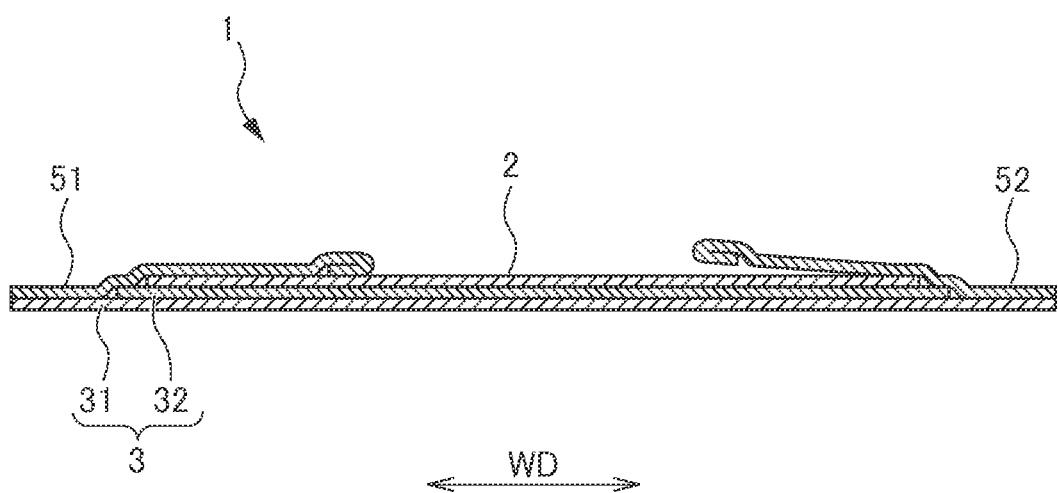
FIG. 6 is a cross-sectional view taken along the line C-C of FIG. 2.

The back sheet 31 is configured in a rectangular shape that is wider than, and has substantially the same length as, the top sheet 2, as shown in FIGS. 4 to 6. The back sheet 31 composes a surface of the absorbent article for pet 1, on a side not in contact with the pet's body.

The waterproof sheet 32 is configured to be smaller in width than the back sheet 31 and greater in width than the top sheet 2 and is arranged on a top sheet 2 side of the back sheet 31.

As the back sheet 31 and the waterproof sheet 32, a hydrophobic nonwoven fabric, a liquid impermeable plastic film, a laminated sheet made of the nonwoven fabric and the liquid impermeable plastic film, an SMS nonwoven fabric made by sandwiching a high-water resistance melt-blown nonwoven fabric with a high-strength spun-bond nonwoven fabric, and the like can be used.

Figure 3:
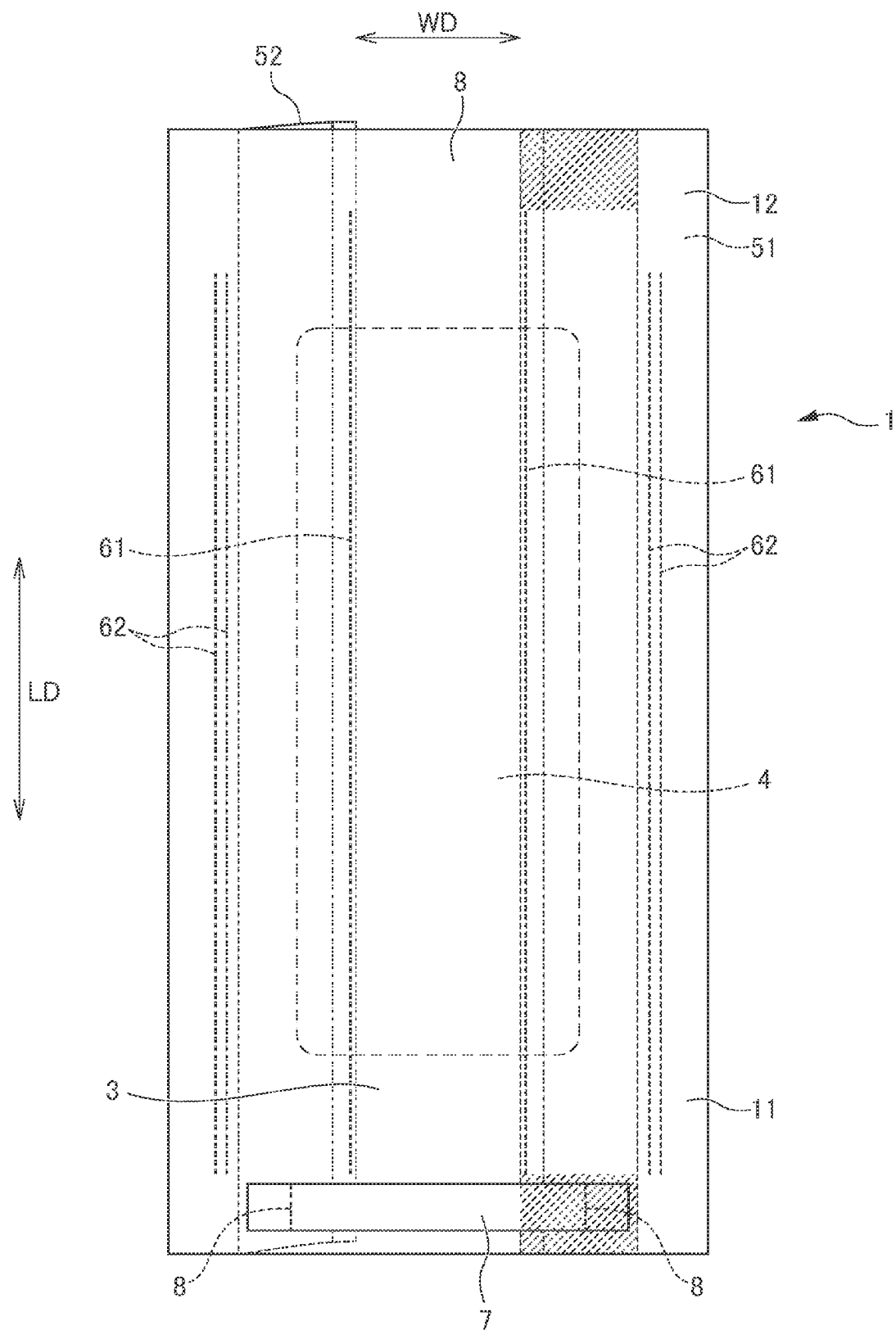
FIG. 3 is a plan view of the absorbent article for pet according to the first embodiment viewed from a back surface layer side.

The absorbent core 4 is arranged between the top sheet 2 and the back surface layer 3 that are layered, as shown in FIG. 4. As shown in FIGS. 2 and 3, the absorbent core 4 is configured in a rectangular shape smaller in width and length than the top sheet 2 and the back sheet 31. As shown in FIGS. 2 and 3, the absorbent core 4 is arranged in a substantially central portion in the width direction of the top sheet 2 and the back sheet 31, from a first end side to a second end side in the longitudinal direction. As the absorbent core 4, fluff pulp and high absorbance polymer wrapped with a core wrapping material such as tissue can be used.

As the fluff pulp used in the absorbent core 4, chemical pulp, cellulose fiber, and artificial cellulose fiber such as rayon, acetate, and the like may be cited. As the high absorbance polymer, granulous or fibrous polymer of starch, acrylic acid, and amino acid may be cited.

The pair of side sheets 51, 52 are configured in an elongated rectangular shape as shown in FIG. 2 and arranged on respective side portions along the longitudinal direction of a body side of the top sheet 2. The pair of side sheets 51, 52 is configured to have substantially the same length as the top sheet 2 and the back sheet 31. As shown in FIGS. 4 to 6, outer edges of the pair of side sheets 51, 52 correspond to side edges of the back sheet 31. The outer edges of the pair of side sheets 51, 52 are joined to the side edges of the back sheet 31.

A part of the inner edges of the pair of side sheets 51, 52 is a free-end, as shown in FIGS. 1 and 5. More specifically, the pair of side sheets 51, 52 include: a front side sheet 51 arranged on a front side of the pet's body when the absorbent article for pet 1 is put on to the pet; and a rear side sheet 52 arranged on a rear side of the pet's body.

The inner edge of the front side sheet 51 is joined to the top sheet 2 in the vicinity of the first end portion 11 arranged on a first end side of the absorbent article for pet 1 in a longitudinal direction LD, and in the vicinity of the second end portion 12 arranged on a second end side, as shown in FIGS. 4 and 6. In addition, the inner edge of the front side sheet 51 is a free end in a portion other than the first end portion and the second end portion of the front side sheet 51 in the longitudinal direction LD, as shown in FIG. 4.

As shown in FIGS. 4 to 6, the inner edge of the rear side sheet 52 is a free end along the overall length of the absorbent article for pet 1 in the longitudinal direction LD.

As the side sheets 51, 52, a water repellent or hydrophobic sheet is preferably used. More specifically, various nonwoven fabrics such as spun lace nonwoven fabric, spun bond nonwoven fabric, thermal bond nonwoven fabric, melt-blown nonwoven fabric, needle-punched nonwoven fabric, air-through nonwoven fabric and the like can be used. As the fiber constituting the nonwoven fabric, synthetic fiber of olefin, polyester, polyamide and the like such as polyethylene and polypropylene; regenerated fiber such as rayon and cupra; and natural fiber such as cotton can be used.

The first elastic member 61 is arranged in the vicinity of each inner edge of the front side sheet 51 and the rear side sheet 52, as shown in FIGS. 1 to 3. More specifically, the first elastic member 61 is sandwiched by the side sheet that is folded back from the inner edge side and fixed to the side sheet by a hotmelt adhesive in an extended state as shown in FIG. 5. The first elastic member 61 is, in the extended state, greater in length than the absorbent core 4 in the longitudinal direction and is arranged on the front side sheet 51 and the rear side sheet 52 as shown in FIGS. 2 and 3.

The second elastic members 62 are arranged in each of the pair of side portions along the longitudinal direction LD of the absorbent article for pet 1, as shown in FIGS. 1 to 3. More specifically, each second elastic member 62 is arranged between the front side sheet 51 and the back sheet 31, and between the rear side sheet 52 and the back sheet 31, respectively, as shown in FIG. 5. In addition, the second elastic members 62 are fixed to the side sheets 51, 52 and the back sheet 31 by a hotmelt adhesive.

The second elastic members 62 are, in the extended state, greater in length than the absorbent core 4 in the longitudinal direction and are arranged on each of the pair of side portions along the longitudinal direction LD of the absorbent article for pet 1.

As the first elastic members 61 and the second elastic members 62, any material that is thin and stretchable can be used, for example: natural rubber such as filiform rubber and flat rubber, or a thermoplastic elastomer such as urethane, ethylene-vinyl acetate copolymer (EVA), PE or the like. More specifically, as the thermoplastic elastomer, polybutadiene, polyisoprene, styrene-butadiene copolymer, styrene-isoprene copolymer, polyurethane, ethylene-vinyl acetate copolymer, ethylene-a-olefin copolymer and the like that are processed to be filiform or formed in a film and then slitted into thin strips may be cited.

The hook tape 7 is arranged on an outer surface of the first end portion 11 (a face on the back surface layer 3 side), as shown in FIGS. 1 to 3. The hook tape 7 is configured in a rectangular shape and arranged such that the longitudinal direction of the hook tape 7 is along a width direction WD of the absorbent article for pet 1. The hook tape 7 is attached to a separate position within a predetermined distance L1 from the side edge of the first end portion 11.

As shown in FIG. 4, the hook tape 7 has a rectangular shaped base portion 71 and a plurality of hook portions 72 provided on one surface of the base portion 71. The hook tape 7 is attached to the back sheet 31 such that the surface, on which the plurality of hook portions 72 are formed, is directed outward.

In the hook tape 7, the base portion 71 and the plurality of hook portions 72 are integrally formed with a synthetic resin material such as polypropylene. From a viewpoint of preferably forming the folding-line portion 8 (to be described later), it is preferable for the hook tape 7 to have predetermined thickness and predetermined bending rigidity. With regard to the bending rigidity when the hook tape 7 is bent in the longitudinal direction (the width direction WD of the absorbent article for pet 1), it is preferable for the bending resistance to be 60 mm to 200 mm, when measured with a bending resistance method A (45-degree cantilever method) as defined in L1084 (testing method for flocked fabrics).

Length W1 of the hook tape 7 in the width direction WD of the absorbent article for pet 1 is configured to be greater than the length W2 of the absorbent core 4 in the width direction.

A distance L1 from the edge of the first end portion 11 to the side edge of the hook tape 7 is preferably 5 mm to 50 mm, and is more preferably 10 mm to 30 mm.

If the distance L1 from the edge of the first end portion 11 to the side edge of the hook tape 7 is below 5 mm, the pet's hair may be caught in the hook tape 7 when the absorbent article for pet 1 is put on the pet.

If the distance L1 from the edge of the first end portion 11 to the side edge of the hook tape 7 exceeds 50 mm, length of pocket portions 14, 15 (to be described later) may not be sufficiently ensured. Moreover, the effective maximum length of the absorbent article for pet 1 (the length from the second end portion 12 to the hook tape 7) may be shortened to narrow the adjustable range in the lengthwise direction when the absorbent article for pet 1 is put on the pet.

Each of a pair of folding-line portions 8 is formed on one end side and another end side of the hook tape 7 in the longitudinal direction thereof, so as to extend in the longitudinal direction LD of the absorbent article for pet 1. The pair of folding-line portions 8 is formed by creasing the hook tape 7, which is configured to be points of folding back from both ends of the hook tape 7 in the longitudinal direction toward the top sheet 2 side. In other words, in a case in which the absorbent article for pet 1 is arranged such that the back surface layer 3 side is an under surface, the first end portion 11 is configured as shown in FIG. 4 such that both end sides of the absorbent article for pet 1 in the width direction WD are bent at the pair of folding-line portions 8 and are raised toward the top sheet 2 side.

As shown in FIG. 2, length between the pair of folding-line portions 8 is configured to be the same as, or wider than, the length W3 of the absorbent core 4.

In the above-described absorbent article for pet 1, the first elastic member 61 in the extended state is fixed to the front side sheet 51 and the rear side sheet 52 along the longitudinal direction LD of the absorbent article for pet 1. In addition, the second elastic members 62 in the extended state are fixed between the side sheets 51, 52 and the back sheet 31, along the longitudinal direction LD of the absorbent article for pet 1.

Given this, the absorbent article for pet 1 in a natural state (without external force applied) has a solid shape as shown in FIG. 1, with the first elastic members 61 and the second elastic members 62 being contracted to thereby bring the first end portion 11 and the second end portion 12 close to each other, with the top sheet 2 side constituting an inner surface. A pair of waist gather portions 13 that are stretchable in the longitudinal direction LD are thus formed on a pair of side portions along the longitudinal direction LD of the absorbent article for pet 1 (see FIG. 1). Free end sides of the front side sheet 51 and the rear side sheet 52 are respectively raised to form a pocket portion 14 between the inner surface of the front side sheet 51 and the outer surface of the top sheet 2, and a pocket portion 15 between the inner surface of the rear side sheet 52 and the outer surface of the top sheet 2 (see FIG. 4).

Figure 7:
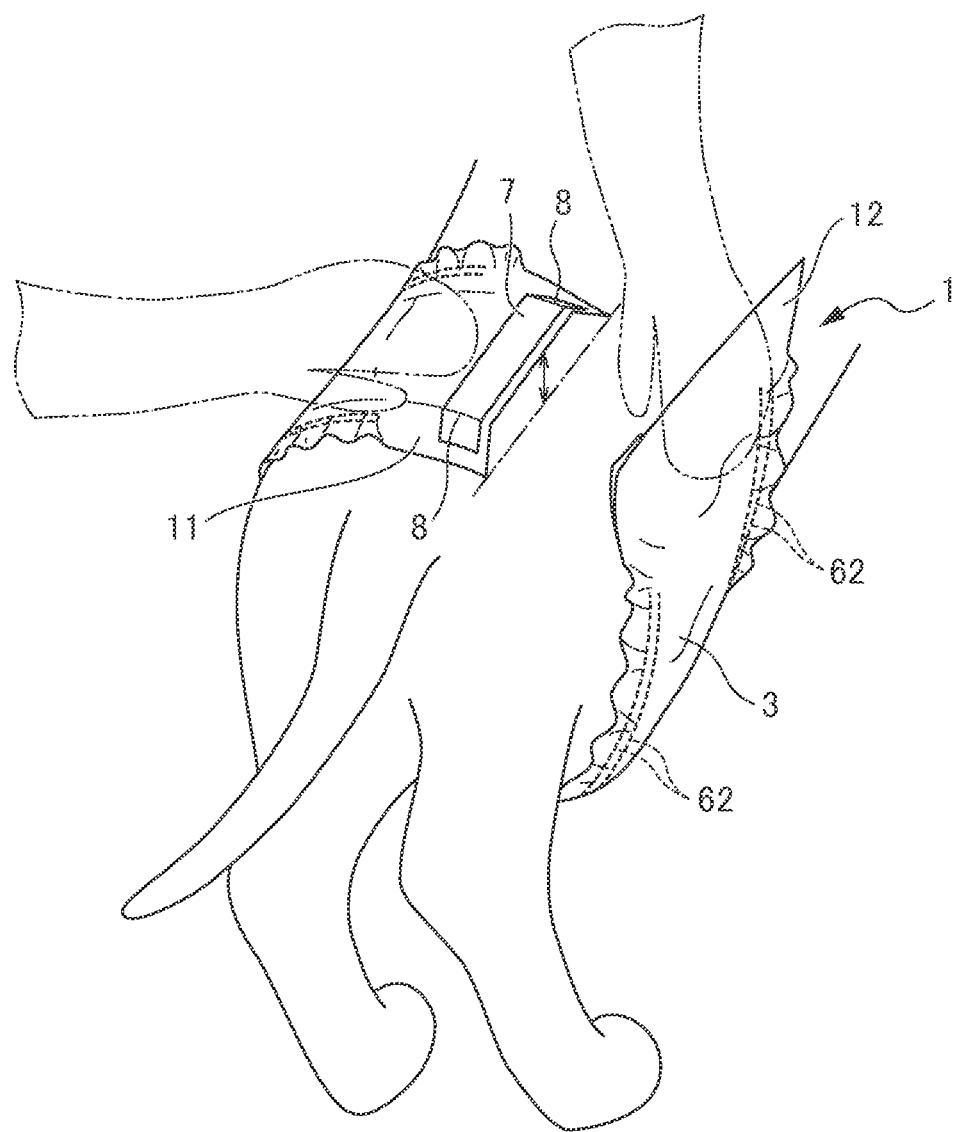
FIG. 7 is a diagram illustrating a process of putting the absorbent article for pet on a pet, in which the first end portion is placed on the pet's back.
Figure 8:
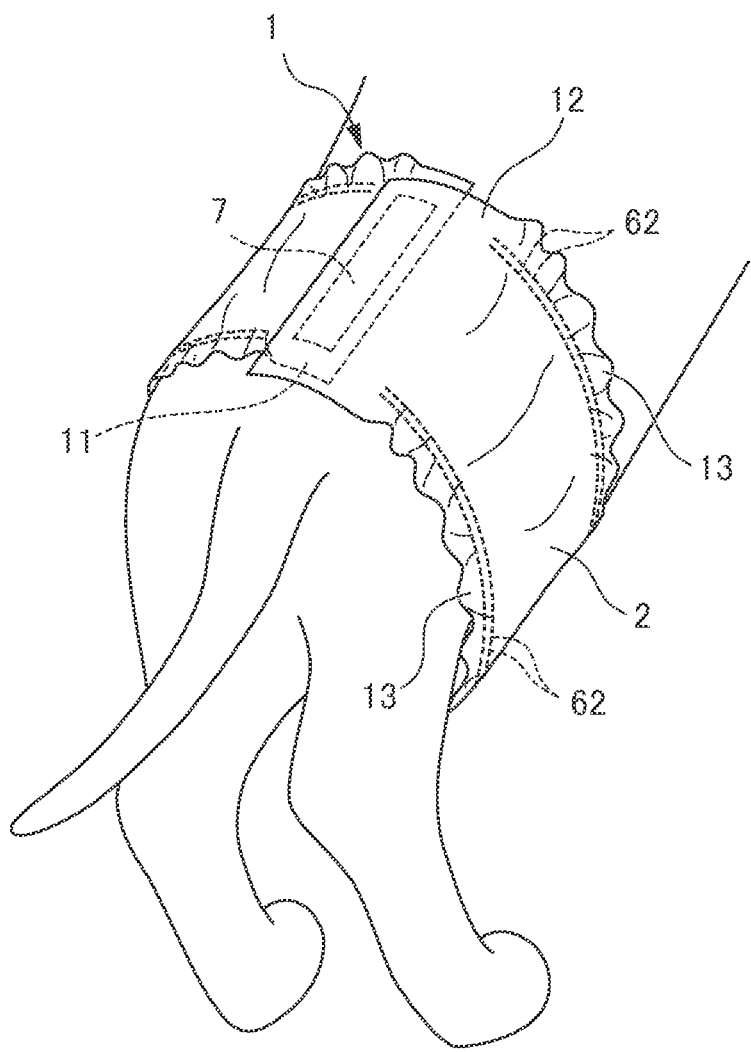
FIG. 8 is a diagram illustrating a state where the absorbent article for pet is put around the pet's waist.
Figure 9:
FIG. 9 is a diagram illustrating the state in FIG. 7 viewed from the pet's side.

Next, steps of putting on the absorbent article for pet 1 according to the first embodiment to a pet will be described with reference to FIGS. 6 to 8. FIGS. 7 to 9 are diagrams illustrating a process of putting on the absorbent article for pet according to the first embodiment to a pet. FIG. 7 is a diagram illustrating a state where the first end portion 11 is placed on the pet's back; and FIG. 8 is a diagram illustrating a state where the absorbent article for pet 1 is put on to the pet's waist. FIG. 9 is diagram illustrating the state in FIG. 7 viewed from the pet's side portion.

First, as shown in FIG. 7, the first end portion 11 of the absorbent article for pet 1 is placed on the pet's back, and the vicinity of the first end portion 11 is held by one hand of a user. Next, in a state where the vicinity of the first end portion 11 is held by one hand, the second end portion 12 of the absorbent article for pet 1 is held by the other hand and wrapped around the pet's body to cover the pet's abdomen.

Subsequently, the second end portion 12 of the absorbent article for pet 1 is pulled to bring the pair of waist gather portions 13 into close contact with the pet's waist.

Subsequently, as shown in FIG. 9, the inner surface of the second end portion 12 (a surface on the top sheet 2 side) of the absorbent article for pet 1 is engaged with the hook tape 7 provided on the outer surface of the first end portion (a surface on the back sheet 31 side). The absorbent article for pet 1 is thus wrapped around the pet's waist.

Here, in the first embodiment, the pair of folding-line portions 8 is formed in the hook tape 7 arranged in the first end portion 11. Both end sides of first end portion 11 of the absorbent article for pet 1 in the width direction WD are bent toward the top sheet 2 side. As a result, in a state where the first end portion 11 of absorbent article for pet 1 is positioned on the pet's back, as shown in FIGS. 7 and 9, a gap is formed between the pet's back and the surface on the top sheet 2 side of the absorbent article for pet 1 (see the arrow in FIGS. 7 and 9). The hook tape 7, in which the pair of folding-line portions is formed, has predetermined bending rigidity. As a result, when the absorbent article for pet 1 is put on, even if the second end portion 12 is pulled from the state where the first end portion 11 of the absorbent article for pet 1 is positioned on the pet's back, the gap formed between the pet's back and the surface on the top sheet 2 side of the absorbent article for pet 1 is maintained.

When the absorbent article for pet 1 is put on the pet by engaging the hook tape 7 with the inner surface of the second end portion 12 (the surface on the top sheet 2 side), the hook tape 7 is depressed by the second end portion 12 and is transformed to be in close contact with the pet's body. As a result, the gap formed between the pet's back and the surface on the top sheet 2 side of the absorbent article for pet 1 disappears, and the absorbent article for pet 1 is preferably put on.

The above-described absorbent article for pet 1 according to the first embodiment provides the following effects.

(1) The rectangular hook tape 7 is provided on the back sheet 31 side of the first end portion 11 so as to extend in the width direction WD of the absorbent article for pet 1, and the pair of folding-line portions 8 is formed in the hook tape 7. As a result, both end sides of the first end portion 11 of the absorbent article for pet 1 in the width direction WD can be bent at the pair of folding-line portions 8 toward the top sheet 2 side; therefore, a gap can be formed between the pet's back and the surface on the top sheet 2 side of the absorbent article for pet 1 in a state where the first end portion 11 of the absorbent article for pet 1 is positioned on the pet's back. Therefore, even if the pet moves in a state where the first end portion 11 is held by one hand to be in close contact with the pet's back, the pet's hair is less likely to be entangled with the hook tape 7 when the absorbent article for pet 1 is put on.

(2) The absorbent article for pet 1 is configured to have a shape contracted in the longitudinal direction in a natural state, by arranging the first elastic members 61 and the second elastic members 62 in the side portions along the longitudinal direction LD of the absorbent article for pet 1. Therefore, the second end portion 12 needs to be strongly pulled such that the absorbent article for pet 1 in a stretched state is made to preferably fit the pet's waist. Accordingly, the pair of folding-line portions 8 is formed in the hook tape 7 having predetermined bending rigidity. As a result, when the absorbent article for pet 1 is put on, even if the second end portion 12 is pulled from the state where the first end portion 11 of the absorbent article for pet 1 is positioned on the pet's back, the shape of the first end portion 11 bent at the folding-line portions 8 can be maintained, and the gap formed between the pet's back and the surface on the top sheet 2 side of the absorbent article for pet 1 can be maintained. Therefore, when the absorbent article for pet 1 is put on, the pet's hair is less likely to be entangled with the hook tape 7.

(3) The length W2 between the pair of folding-line portions 8 is configured to be larger than the width W3 of the absorbent core 4. As a result, the gap formed between the pet's back and the surface on the top sheet 2 side of the absorbent article for pet 1 can be made large in the width direction WD of the absorbent article for pet 1. Therefore, entanglement of the pet's hair can be prevented in a wide range of the hook tape 7.

(4) The hook tape 7 is arranged within the predetermined distance L1 from the edge of the first end portion 11. As a result, in a state where the first end portion 11 is positioned on the pet's back, even if the pet's hair covers the outer surface of the first end portion 11 due to movement or the like of the pet, the pet's hair is less likely to be entangled with the hook tape 7. Therefore, the wearability of the absorbent article for pet 1 can be further improved.

Figure 10A:
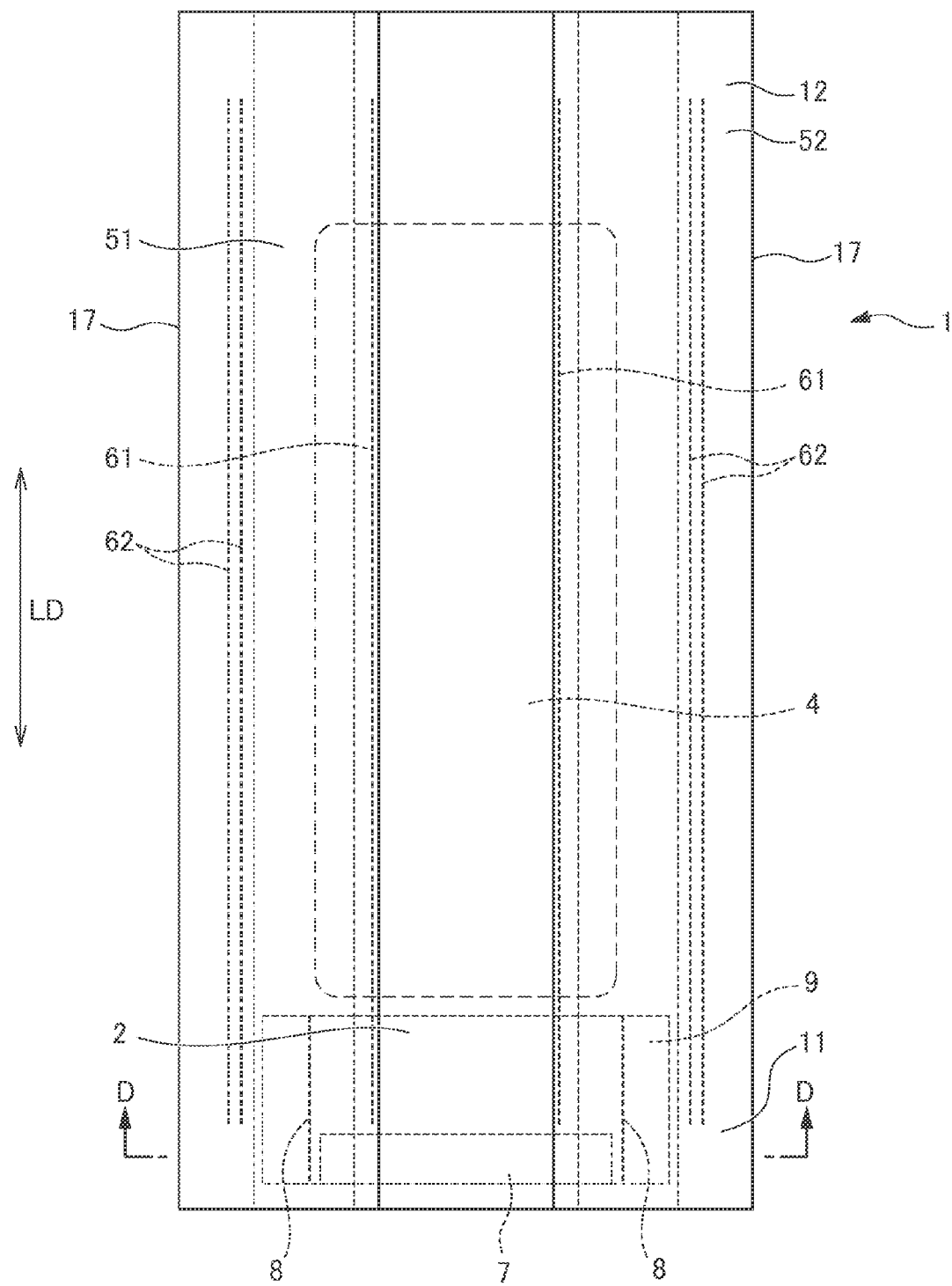
FIG. 10A is a plan view of the absorbent article for pet according to a second embodiment viewed from the top surface layer side.

Next, an absorbent article for pet 1 according to a second embodiment will be described with reference to FIGS. 10A and 10B. FIG. 10A is a plan view of the absorbent article for pet 1 according to the second embodiment viewed from the top sheet side; and FIG. 10B is a sectional view taken along the line D-D of FIG. 10A.

In the description of the following embodiments, the same constituent features are referred by the same reference numerals and a description thereof is omitted or simplified.

The absorbent article for pet 1 according to the second embodiment differs from the first embodiment mainly in the configuration of a pair of folding-line portions 8.

Figure 10B:
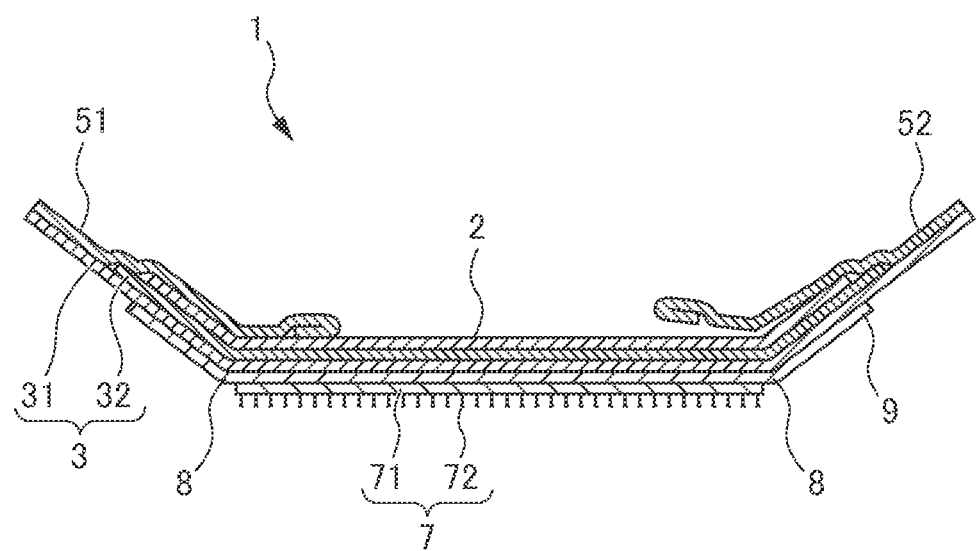
FIG. 10B is a cross-sectional view taken along the line D-D of FIG. 10A.

In the second embodiment, as shown in FIG. 10B, a rectangular base material 9 is arranged in a first end portion 11. The base material 9 is configured as a plate made of a synthetic resin material such as polypropylene. The base material 9 is arranged on an outer surface of a back sheet 31 of the first end portion 11. A hook tape 7 is arranged on an outer surface of the base material 9.

From a viewpoint of preferably forming the folding-line portions 8, it is preferable for the base material 9 to have predetermined thickness and predetermined bending rigidity. With regard to the bending rigidity of the base material 9 being bent in the longitudinal direction (the width direction WD of the absorbent article for pet 1), it is preferable for the bending resistance to be 60 mm to 200 mm, which is measured with a bending resistance method A (45-degree cantilever method) as defined in L1084 (testing method for flocked fabrics).

The length of the base material 9 in the width direction WD of the absorbent article for pet 1 is configured to be greater than the length of the absorbent core 4 in the width direction.

In the second embodiment, the pair of folding-line portions 8 is formed in the base material 9. As shown in FIG. 10A, the length between the pair of folding-line portions 8 is configured to be the same or greater than the length of the absorbent core 4.

The absorbent article for pet 1 according to the second embodiment provides the following operational effects, in addition to the above operational effects (3) and (4).

(5) The base material 9 is arranged on the back sheet 31 side of the first end portion 11, and the pair of folding-line portions 8 is formed in the base material 9. As a result, both end sides of the first end portion 11 of the absorbent article for pet 1 in the width direction WD can be bent at the pair of folding-line portions 8 toward the top sheet 2 side; therefore, a gap can be formed between the pet's back and the surface on the top sheet 2 side of the absorbent article for pet 1 in a state where the first end portion 11 of the absorbent article for pet 1 is positioned on the pet's back. Therefore, even if the pet moves in a state where the first end portion 11 is held by one hand to be in close contact with the pet's back, the pet's hair is less likely to be entangled with the hook tape 7 when the absorbent article for pet 1 is put on.

(6) The absorbent article for pet 1 is configured to have a shape contracted in the longitudinal direction in a natural state, by arranging the first elastic members 61 and the second elastic members 62 in the side portions along the longitudinal direction LD of the absorbent article for pet 1. Therefore, the second end portion 12 needs to be strongly pulled such that the absorbent article for pet 1 in a stretched state is made to preferably fit the pet's waist. Accordingly, the pair of folding-line portions 8 is formed in the base material 9 having predetermined bending rigidity. As a result, when the absorbent article for pet 1 is put on, even if the second end portion 12 is pulled from the state where the first end portion 11 of the absorbent article for pet 1 is positioned on the pet's back, the shape of the first end portion 11 being bent at the folding-line portions 8 can be maintained, and the gap formed between the pet's back and the surface on the top sheet 2 side of the absorbent article for pet 1 can be maintained. Therefore, when the absorbent article for pet 1 is put on, the pet's hair is less likely to be entangled with the hook tape 7.

Figure 11A:
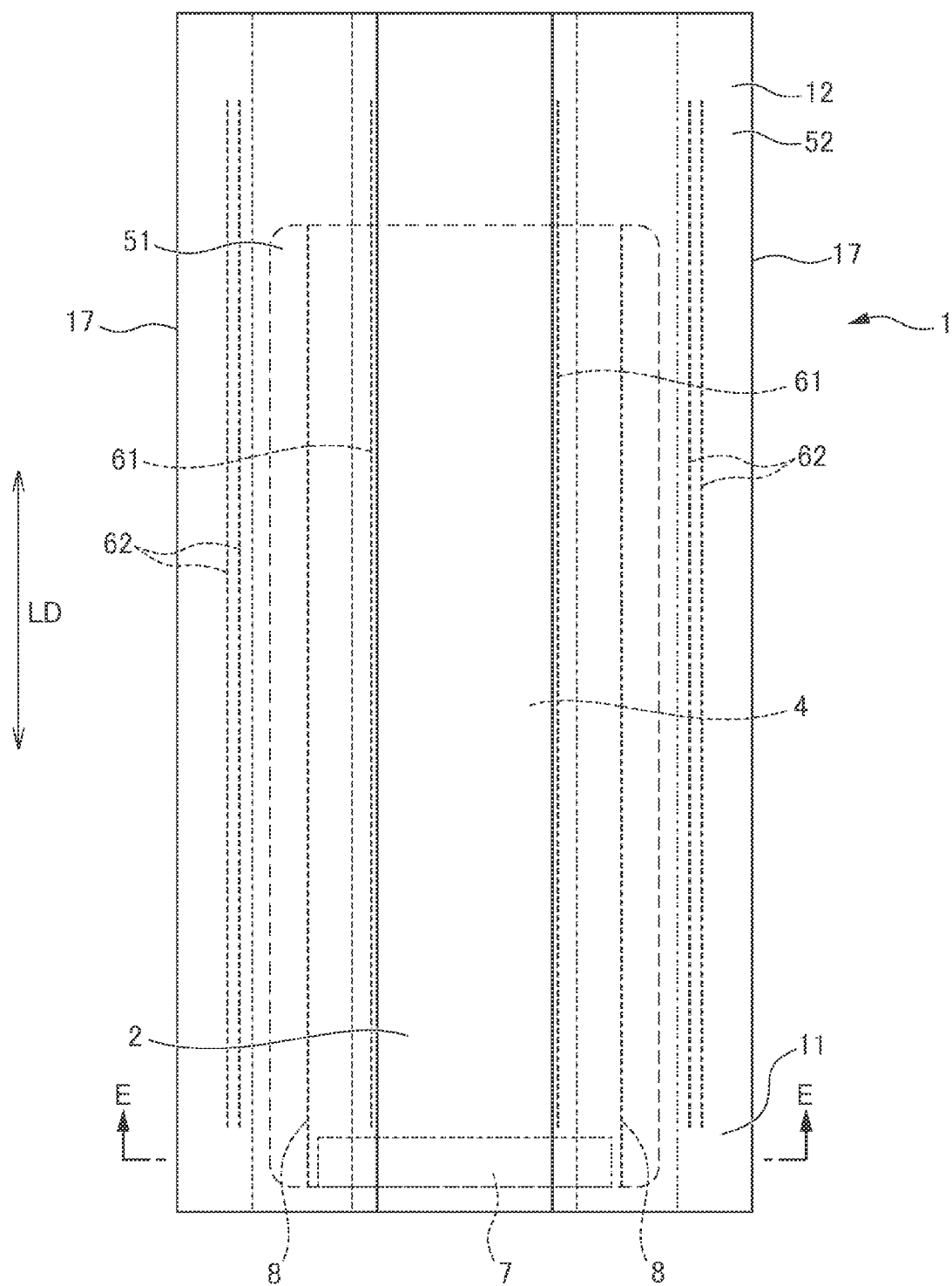
FIG. 11A is a plan view of the absorbent article for pet according to a third embodiment viewed from the top surface layer side.
Figure 11B:
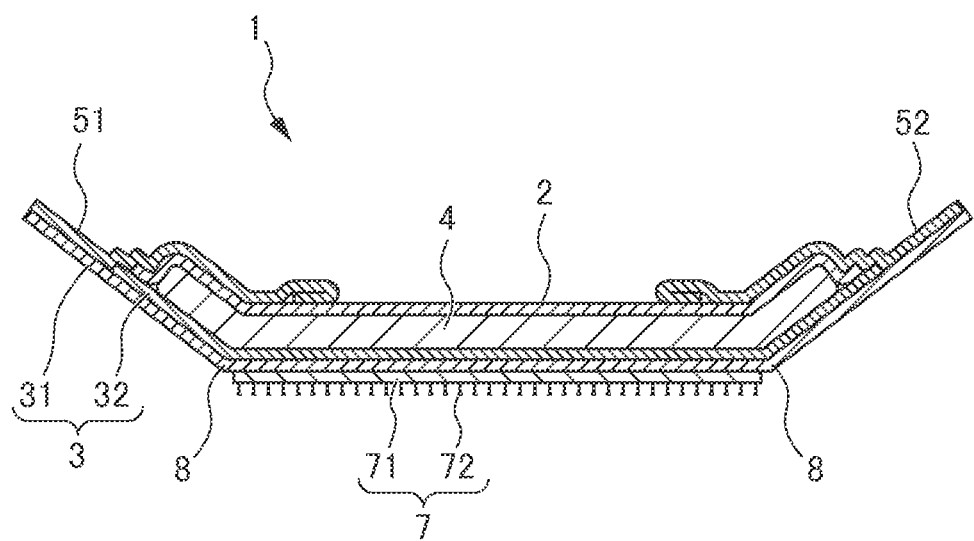
FIG. 11B is a cross-sectional view taken along the line E-E of FIG. 11A.

Next, an absorbent article for pet 1 according to a third embodiment will be described with reference to FIGS. 11A and 11B. FIG. 11A is a plan view of the absorbent article for pet 1 according to the third embodiment viewed from the top sheet side; and FIG. 11B is a sectional view taken along the line E-E of FIG. 11A.

The absorbent article for pet 1 according to the third embodiment differs from the first embodiment mainly in a pair of folding-line portions 8 being formed in an absorbent core 4.

In the third embodiment, as shown in FIG. 11A, the absorbent core 4 is arranged to extend to a vicinity of a first end portion 11. The pair of folding-line portions 8 is formed by creasing the absorbent core 4.

In the third embodiment, the length of the hook tape 7 in the width direction WD of the absorbent article for pet 1 is configured to be smaller than the width of the absorbent core 4. The folding-line portions 8 are not formed in the hook tape 7.

The absorbent article for pet 1 according to the third embodiment provides the following operational effects, in addition to the above operational effects (4).

(7) The absorbent core 4 is arranged to extend to the vicinity of the first end portion 11, and the pair of folding-line portions 8 is formed in the absorbent core 4. As a result, both end sides of the first end portion 11 of the absorbent article for pet 1 in the width direction WD can be bent at the pair of folding-line portions 8 toward the top sheet 2 side; therefore, a gap can be formed between the pet's back and the surface on the top sheet 2 side of the absorbent article for pet 1 in a state where the first end portion 11 of the absorbent article for pet 1 is positioned on the pet's back. Therefore, even if the pet moves in a state where the first end portion 11 is held by one hand to be in close contact with the pet's back, the pet's hair is less likely to be entangled with the hook tape 7 when the absorbent article for pet 1 is put on.

(8) The absorbent article for pet 1 is configured to have a shape contracted in the longitudinal direction in a natural state, by arranging the first elastic members 61 and the second elastic members 62 in the side portions along the longitudinal direction LD of the absorbent article for pet 1. Therefore, the second end portion 12 needs to be strongly pulled such that the absorbent article for pet 1 in a stretched state is made to preferably fit the pet's waist. Accordingly, the pair of folding-line portions 8 is formed in the absorbent core 4 which is thick and has high bending rigidity. As a result, when the absorbent article for pet 1 is put on, even if the second end portion 12 is pulled from the state where the first end portion 11 of the absorbent article for pet 1 is positioned on the pet's back, the shape of the first end portion 11 being bent at the folding-line portions 8 can be maintained, and the gap formed between the pet's back and the surface on the top sheet 2 side of the absorbent article for pet 1 can be maintained. Therefore, when the absorbent article for pet 1 is put on, the pet's hair is less likely to be entangled with the hook tape 7.

The preferred embodiments of the present invention have been described above; however, the present invention is not limited thereto and can be modified as appropriate.

For example, in the first embodiment, the hook tape 7 is arranged on the outer surface of the first end portion 11, and the pair of folding-line portions 8 is formed in the hook tape 7; however, the present invention is not limited thereto. In other words, by applying an adhesive to a surface of a sheet-like base material having predetermined bending rigidity to make an adhesive tape, the adhesive tape may be arranged on the outer surface of the first end portion, and a pair of folding-line portions may be formed in the adhesive tape. In this case, the inner surface of the second end portion may be constituted of a film material that cannot be engaged with the hook member.

In each of the above embodiments, the inner edges of both sides of the front side sheet 51 in the longitudinal direction LD are joined to the top sheet 2, and the inner edges of the rear side sheet 52 are not joined to the top sheet 2; however, the present invention is not limited thereto. In other words, all the inner edges of both sides of the front side sheet and the rear side sheet in the longitudinal direction LD may be joined to the top sheet.

In each of the above embodiments, the back surface layer 3 is constituted of two layers including the back sheet 31 and the waterproof sheet 32; however, the present invention is not limited thereto. In other words, the back surface layer can also be constituted of only the back sheet or the waterproof sheet.

The invention claimed is:

1. An absorbent article for pet, comprising:
   a liquid permeable top surface layer;
   a liquid impermeable back surface layer;
   an absorbent core positioned between the top surface layer and the back surface layer;
   a first end portion and a second end portion of the absorbent article for pet configured in a rectangular shape, opposed to each other;
   a pair of side portions opposed to each other and orthogonal to the first and second end portions, and wherein, in a state of being wrapped around a pet's waist, a top surface layer side of the first end portion is arranged to face the pet's body, and the top surface layer side of the second end portion is removably attached to a back surface layer side of the first end portion,
   a locking member positioned on the back surface layer side of the first end portion, and formed in a rectangular shape, wherein a longitudinal direction of the locking member extends along a width direction of the absorbent article for pet; and
   a pair of folding-line portions formed in the first end portion, which pair of folding-line portions includes a folding-line portion formed in a side end of the first end portion in the width direction of the absorbent article and another folding-line portion formed in an opposite side end of the first end portion in the width direction with no folding-lines between the pair of folding-line portions, wherein a pair of side portions of the first end portion are bent at the pair of folding-line portions toward the top surface layer side, and length between the pair of folding-line portions is larger than the width of the absorbent core.

2. The absorbent article for pet according to claim 1, wherein
   the pair of folding-line portions is formed in the locking member, and extends along a longitudinal direction of the absorbent article for pet.

3. The absorbent article for pet according to claim 1, further comprising:
   a pair of side sheets arranged on an outer surface side of the top surface layer in the pair of side portions along the longitudinal direction of the absorbent article for pet, wherein an outer edge is joined to the top surface layer or the back surface layer, and at least a part of an inner edge is a free end;
   a pair of first elastic members arranged in a stretched state in a vicinity of the inner edge of the pair of side sheets; and
   a pair of pocket portions formed between an inner surface of the pair of side sheets and an outer surface of the top surface layer.

4. The absorbent article for pet according to claim 1, further comprising a pair of second elastic members arranged in a stretched state in each of the pair of side portions.

5. The absorbent article for pet according to claim 1, wherein
   the locking member is attached at a separated position within a predetermined distance from a side edge of the first end portion.

6. The absorbent article for pet according to claim 1, further comprising a rectangular base material arranged in the first end portion, wherein the pair of folding-line portions is formed in the base material.

7. The absorbent article for pet according to claim 1, wherein
   bending resistance, with regard to bending rigidity of the locking member being bent in a longitudinal direction, is 60 mm to 200 mm, which is measured with a bending resistance method A (45-degree cantilever method) as defined in L1084 (testing method for flocked fabrics).

* * * * *